US00PP08344P

United States Patent [19]

Skelton

[11] Patent Number: Plant 8,344

[45] Date of Patent: Aug. 10, 1993

[54] "SKELTON" KIWIFRUIT PLANT

[76] Inventor: Donald A. Skelton, Maraeorahia Road, RD 3, Waiuku, New Zealand

[21] Appl. No.: 778,038

[22] Filed: Oct. 16, 1991

[51] Int. Cl.[5] ..... A01H 5/00
[52] U.S. Cl. ..... Plt./33.1
[58] Field of Search ..... Plt./33.1; 800/200, 800/DIG. 9

[56] References Cited

U.S. PATENT DOCUMENTS

P.P. 6,815 5/1989 Wilkins et al. ..... Plt./33/1

*Primary Examiner*—James R. Feyrer
*Attorney, Agent, or Firm*—Quarles & Brady

[57] ABSTRACT

A new and distinct variety of Kiwifruit is described. The variety results from controlled pollination of *Actinidia deliciosia* Blue, a male selection of unkown parentage, and *Actinidia deliciosia* L513, a female selection. The variety is distinguished by its generally obovoid fruit shape, early fruit maturity, and medium to strong vigour. The new variety has been named "Skelton."

1 Drawing Sheet

BACKGROUND OF THE INVENTION

The present invention relates to a new and distinctive Kiwifruit cultivar having a generally obovoid shaped fruit. More particularly, the new cultivar is designated 'Skelton'.

The variety was bred in 1980 on the inventor's properties by the inventor on his property at Waiuku, New Zealand and is a result of controlled pollination of *Actinidia deliciosia* Blue, a male selection of unknown parentage, and *Actinidia deliciosia* L513, a female selection. Blue was selected as the pollen parent for Skelton because of its strong growth and very early flowering, while the L513 seed parent was selected for its early maturity, large fruit, shape and size. Both parents are proprietary lines maintained by the inventor and are not available to the public in commerce.

The plant was reproduced by grafting onto Bruno rootstock (seedlings from the seed of the Bruno plant. The seedlings used were Matua/Bruno). Asexual propagation shows that the unique combination of characteristics come true to form and are established and transmitted through succeeding propagations. The new variety has been named the 'Skelton' variety.

SUMMARY OF THE INVENTION

The present invention relates to a new and distinct kiwifruit variety. More particularly, the variety is designated 'Skelton' and is derived from a cross between a male *Actinidia deliciosia* Blue and a female *Actinidia deliciosia* L513. The Skelton variety exhibits medium to strong vine vigor, early fruit maturity, and large, generally obovoid fruit shape.

The 'Skelton' variety was asexually reproduced by grafting onto 'Bruno' rootstock. Upon asexual reproduction, the distinct combination of characteristics of 'Skelton' come true to form and are established and transmitted through succeeding propagations. The distinctive characteristics of this new kiwifruit cultivar described in detail below were observed in 1989–1990. The age of the plants was about one to two years from graft.

BRIEF DESCRIPTION OF THE DRAWINGS

The invention may be more fully understood by having reference to the accompanying colour photographic reproductions wherein.

BOTANICAL DESCRIPTION OF THE PLANT

The distinctive characteristics of this new kiwifruit cultivar, summarized in Table 1 and described in detail below, were observed in 1989–1990 at the inventor's property at Waiuku, New Zealand. The age of the plants was about 1 to 2 years from graft.

The colour designations herein after set forth are according to the Pantone Colour Formula Guide 7474XR.

TABLE 1

| | Differences from Hayward | |
|---|---|---|
| | 'Hayward' | 'Skelton' |
| Fruit shape | squat | long |
| Fruit maturity | late | early |
| Vine Vigour | medium | medium-strong |
| | **Differences from Bruno** | |
| | 'Bruno' | 'Skelton' |
| Fruit shape | cylindrical | pointed oval |
| Fruit maturity | medium-late | early |
| | **Differences from Gracie** | |
| | 'Gracie' | 'Skelton' |
| Fruit shape | shorter/bulkier | longer/narrower |
| Fruit maturity | medium | early |

The fruit is substantially obovoid in shape but has a circular cross-section typical of the 'Hayward' and 'Bruno' varieties. The length to width ratio is 2:1 as in the 'Bruno' variety. In contrast, 'Skelton' is notably longer in shape than 'Hayward'. Furthermore, 'Skelton' differs from two other "long-shaped" kiwifruit, 'Bruno' and 'Gracie' in a number of characteristics set forth in Table 1. Table 2 presents for comparison the fruit size measurements and length-width ratios of the fruit of the 'Hayward,' 'Bruno' and 'Skelton' varieties.

TABLE 2

| | Average Length | Average Width | Length:Width Ratio | Width:Length Ratio |
|---|---|---|---|---|
| Hayward | 2.87 in | 2.37 in | 1.210 | 0.825 |
| Skelton | 4.13 in | 2.00 in | 2.065 | 0.484 |
| Bruno | 3.55 in | 1.74 in | 2.040 | 0.490 |

The apex shape is truncated. The length of the hair is mainly long as in the 'Hayward' and 'Bruno' varieties and the density is medium as in 'Hayward' and 'Bruno'. The stylar periphery is rounded as in 'Bruno'. The size of the columella in median cross-section is medium (3:1). The shape of the columella in cross-section is only slightly fluted i.e. 1:8 whereas 'Hayward' are nearly all fluted. The colour of the fruit (at 14% Brix) is: Skin, light-mid brown, 465U; Flesh, green, 391U; Core, very pale green, 5875C; Seed, dark brown, 4975U. The fruit colour advances from green to brown with maturity and varies according to the amount of sunlight reaching the fruit. At peak ripeness, the flesh colour is a little lighter than 'Hayward,' and noticeably lighter than 'Bruno.' The fruit has a softer "mouth feel" and a sweeter, less acid taste compared with 'Hayward.'

Good-sized fruit contain 700–900 seeds, a medium count relative to 'Hayward' which contains 1,000–1,400.

The fruit virtually lacks the 'Hayward' mark. The 'Hayward' mark is a shallow sunken line running down the side of the fruit, sometimes ending in a hook or protuberance. It is caused by a stamen sticking to the fruit and the hook by an anther sticking. While this occurs in most *Actinidia deliciosia* varieties it is much more prevalent in 'Hayward.'

Figure 1:
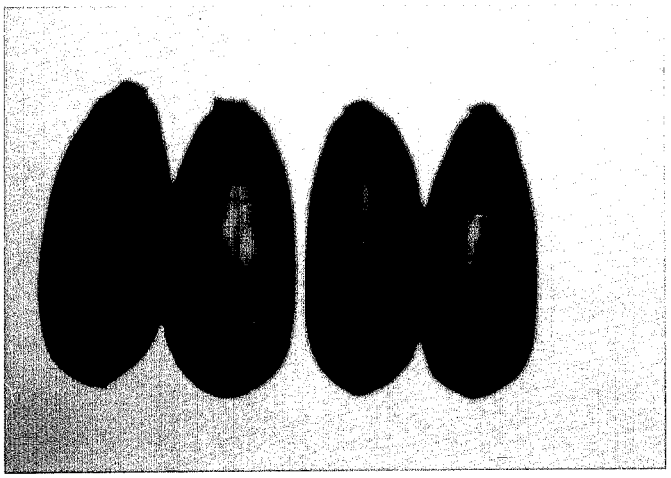
FIG. 1 shows four fruit of the 'Skelton' variety.
Figure 2:
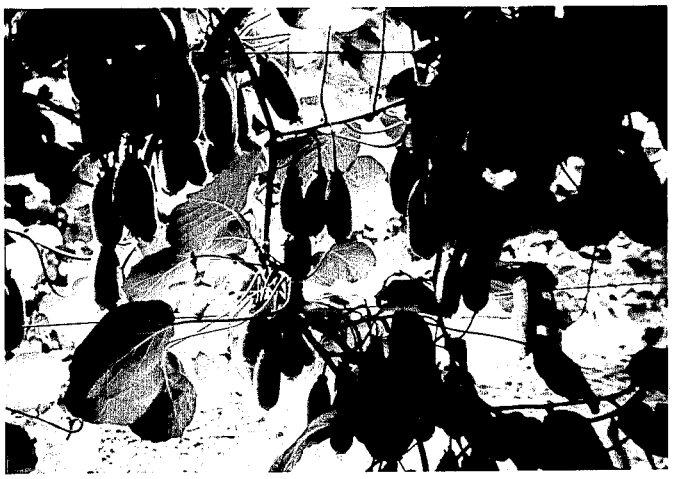
FIG. 2 shows a typical collection of fruit on a vine 30 months from graft.
Figure 3:
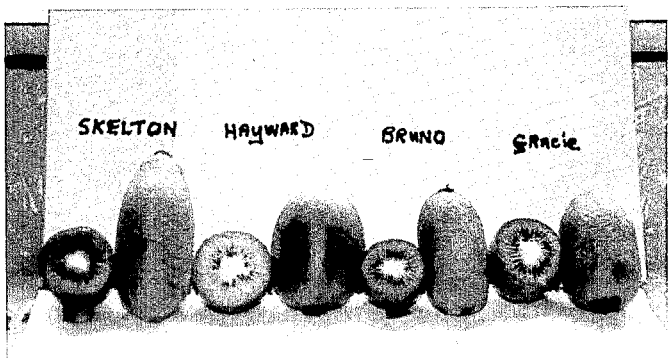
FIG. 3 shows a typical mature fruit of the 'Skelton' variety next to 'Hayward' fruit, 'Bruno' fruit, and 'Gracie' fruit of similar maturity. The photograph is taken prior to the mature harvest stage.

The mean size of mature fruit changes little with advancing harvest season. The fruit depicted in FIG. 3 is taken prior to the mature harvest stage. The harvest season is relatively short due to quickly increasing brix levels.

The time of maturity for harvest is early. This time is reached when the average soluble solids content of a sample of at least ten fruit from five vines (measured using a refractometer) reaches 6.2% ss. Based on a Brix test (6.2% ss) the earliest maturity date, measured over a ten year period of fruit grown on properties at Waipipi and Waiuku, New Zealand, was about March 16 the lastest maturity date was March 25. Hayward, on the same properties, reached 6.2% ss between May 3 and 14. The size of the fruit is reasonably consistent with weights ranging from the smallest 80 gms to 138 gms. The majority of fruit was in the 110 g to 120 gm size range. The average weight from the sample picked (20 fruit) was 115 gm whereas the 'Hayward' sample only averaged 102 gm. There was little variation in the shape of the fruit observed.

The fruit storage is good. The period of viable storage is shorter than the 'Hayward' variety. Trials have shown storage at 0° C. and relative humidity of 85% satisfactory to six months. The shipping qualities are satisfactory and comparable to 'Hayward.' Chilling requirements are similar, but marginally less than 'Hayward.'

After-ripening characteristics differ from 'Hayward,' the new variety having a relatively quick softening ripening to eating stage when compared with 'Hayward.'

PLANT

The plant demonstrates a female sex expression. It has a medium vigour. The plant is deciduous. Frost-hardiness is similar to 'Hayward' and others.

A lateral shoot was observed two months after flowering on internodes of four to eight inches from the tip of growing shoots. The anthocyanin colouration of hairs was brown as in the 'Hayward' variety. The hairs were of medium density as in the 'Hayward' variety.

The central third of a stem of a dormant cane was observed after leaf fall. The colour was yellowish/-brown as in the 'Bruno' variety. The number of lenticels was few, as in the 'Hayward' variety, and of raised conspicuousness. In comparison with the 'Hayward' variety the lenticels on mature canes were larger and more raised.

The colour of the wood is: End of season cane (7 months), brown, 4635U, 2 year old wood, grey, 402U.

The pruning and training requirements are similar to the 'Hayward' variety with one exception: Replacement can should not be stopped or tipped or pruned, as this leads to premature bud burst.

A mature leaf was observed near the base of current seasons growth on sufficiently mature, but not old leaves. It had a generally oblate blade, as in the 'Hayward' variety, and a cuspidate apex, as in the 'Bruno' variety. The base was cordate, as in the 'Hayward' and 'Bruno' varietiies. The margin was crenulate, as in the 'Hayward' and 'Bruno' varieties, this was mainly due to hairs on the margin. The density of hair on the main veins on the lower side of the leaf was medium as in 'Hayward'. The density of stellate hair between the main veins on the lower side was dense as in 'Hayward'. The anthocyanin colouration of the petiole was strong. The leaf colouration was: Mature leaf (8 to 12 inches across), dark green, 574C; Medium leaf (4 inches across), dark green, 371C; Young leaf (2 inches across), dark olive green, 378C.

The flowers were observed when 65 to 75% were in bloom. The time of beginning of flowering was medium as in the 'Bruno' variety. The number of flowers was medium as in the 'Hayward' variety. The length of the pedicel was long (average about 2½ inches). The number of petals was generally six. The length of the petal was meidum as in 'Hayward' and 'Bruno' (about ¾–1½ inches).

The width of the petal was medium as in 'Hayward' (about ¾–1 1/5 inches). The petals were touching a in 'Bruno'. The corolla form was cupped as in 'Hayward' and 'Bruno'. The curvature of the petals was between flat and involute. The attitudee of styles were curved below the middle and none were erect, very distinct from 'Hayward'.

The productivity has been compared with 'Hayward.' Initial preliminary results show 21% more flowers and 35% higher total fruit weight than 'Hayward.' A major difference is the fruiting at a young age (precocity) of 'Skelton' with a full crop in the third season from grafting.

A male variety which blooms in the same period as "Skelton," such as "Derek," is likely to be suitable as a pollinator variety.

I claim:

1. The new and distinct variety of kiwifruit plant herein described and illustrated, and identified by the characteristics enumerated above.

* * * * *